United States Patent [19]

Shannon et al.

[11] Patent Number: 5,431,185
[45] Date of Patent: Jul. 11, 1995

[54] MANIFOLD FOR INFUSING MEDICAL FLUIDS

[75] Inventors: William M. Shannon, Rancho Santa Fe; Donald H. Koenig, San Diego, both of Calif.

[73] Assignee: Pacific Device Inc., San Diego, Calif.

[21] Appl. No.: 275,817

[22] Filed: Jul. 15, 1994

Related U.S. Application Data

[63] Continuation of Ser. No. 59,188, Apr. 13, 1993, abandoned, which is a continuation of Ser. No. 934,163, Aug. 21, 1992, abandoned.

[51] Int. Cl.⁶ ............................................. A61M 37/00
[52] U.S. Cl. ...................................... 137/512.4; 137/605; 604/83; 604/247
[58] Field of Search ................. 137/512.4, 605, 606; 604/83, 247

[56] References Cited

U.S. PATENT DOCUMENTS

| | | | |
|---|---|---|---|
| 3,889,710 | 6/1975 | Brost | 137/512.15 |
| 4,084,606 | 4/1978 | Mittleman | 137/512.4 X |
| 4,181,146 | 1/1980 | Goglio | 137/854 |
| 4,210,173 | 7/1980 | Choski et al. | 137/854 X |
| 4,246,932 | 1/1981 | Raines | 137/512 |
| 4,286,628 | 9/1981 | Paradis et al. | 137/843 |
| 4,310,017 | 1/1982 | Raines | 137/533 |
| 4,369,812 | 1/1983 | Paradis et al. | 137/843 |
| 4,415,003 | 11/1983 | Paradis et al. | 137/843 |
| 4,447,230 | 5/1984 | Gula et al. | 604/247 X |
| 4,535,820 | 8/1985 | Raines | 137/854 |
| 4,620,846 | 11/1986 | Goldberg et al. | 604/28 |
| 4,666,429 | 5/1987 | Stone | 137/605 X |
| 4,749,003 | 6/1988 | Leason | 137/854 |
| 4,781,707 | 11/1988 | Boehringer et al. | 604/317 |
| 4,908,018 | 3/1990 | Thomsen | 604/83 |
| 4,915,688 | 4/1990 | Bischof et al. | 604/83 |
| 4,925,444 | 5/1990 | Orkin et al. | 604/80 |
| 4,966,199 | 10/1990 | Ruchke | 137/843 |
| 5,041,087 | 8/1991 | Loo et al. | 604/83 |
| 5,070,905 | 12/1991 | Paradis | 137/606 |
| 5,078,699 | 1/1992 | Haber et al. | 604/250 |
| 5,095,938 | 3/1992 | Garrison | 137/510 |
| 5,190,524 | 3/1993 | Wex | 604/80 |
| 5,190,525 | 3/1993 | Oswald et al. | 604/83 |
| 5,192,269 | 3/1993 | Poli et al. | 604/82 |

OTHER PUBLICATIONS

Pacific Device Inc. "Other Manifold Designs", Date Unknown.

Primary Examiner—John Rivell
Attorney, Agent, or Firm—Fulwider Patton Lee & Utecht

[57] ABSTRACT

A fluid manifold includes a housing having a first inlet and an outlet and a plurality of inlets intermediate the first inlet and the outlet which are provided with check valve action to prevent retrograde flow through the valved inlets, yet allow individual inlets to pass fluid when the fluid pressure in any individual inlet exceeds that of the interior of the chamber by a predetermined cracking pressure. The check valve action is provided by a single resilient backcheck member which is deformably urged against annular valve seats by support members embodied in the housing opposite and central to the valved inlets. A conventional injection site may be provided in the housing so that additional fluids may be injected into the interior of the manifold through an inserted cannula. A chamber within the manifold is configured to direct a flowstream through the manifold onto and around the resilient backcheck member and all interior surfaces, eliminating dead space where air or fluids may collect, and enhancing flushing of the manifold. This enables simultaneous or sequential administration of multiple medicaments in low volume applications.

5 Claims, 3 Drawing Sheets

MANIFOLD FOR INFUSING MEDICAL FLUIDS

This application is a continuation of application Ser. No. 08/059,188, filed Apr. 13, 1993, now abandoned, which is a continuation of application Ser. No. 07/934,163, filed Aug. 21, 1992, now abandoned.

BACKGROUND OF THE INVENTION

This invention relates generally to infusion sets for use in connection with administration of fluids to a patient and, more particularly, the invention relates to an improved fluid manifold for use in such infusion sets.

Often in the care of a patient, it is desirable to administer medicaments of different types, simultaneously or sequentially, through a single intravenous catheter for example. This is often done by connecting various fluid reservoirs by means of flexible tubing and y-connectors to a single flexible tubing line leading to a venipuncture site in the patient. Also, preparation of a mixture of multiple medicaments in a single reservoir for subsequent infusion into a patient is sometimes done using such an infusion set.

This and other similar means of connecting various fluid sources to a single line have often been found to be cumbersome, and difficult for the medical care personnel to assemble, purge of air, and maintain. The administration of small doses of particular medicaments is inconvenient, involving manipulation of flows in the various lines and adjustment of relevant heights of the reservoirs for example, to assure proper dosage. Moreover, in certain circumstances medicaments in their respective reservoirs can become contaminated by incompatible medicaments from other reservoirs connected in the administration set due to retrograde flow.

These problems having been recognized, it was found that placing stopcocks or check valves in the fluid delivery system at critical points was useful in preventing unwanted retrograde flow and facilitating sequential fluid delivery. Also, toward the goal of streamlining the task of intravenous infusion of multiple differing fluids, manifolds for interconnection of various fluid sources have been used. Some of these manifolds incorporate check valves or stopcocks at the inlets to prevent retrograde flow. These manifolds may be used in intravenous infusion sets for direct infusion of a patient, or for mixing various medicaments into one reservoir for subsequent infusion of a patent.

In pharmacological applications, manifolds have been used to mix differing fluids in preparing various medicaments. Such manifolds have incorporated check valves preventing retrograde flow integral with, and contained within the manifold. Multiple tubing inlets convey differing fluids into the manifold in relatively high volume where they are mixed by turbulence and then exit the manifold through a single outlet.

However, the incorporation of all the various components, including check valves for example, into a single manifold in order to enable connection of multiple fluid sources has not escaped all of the problems associated with prior non-manifold devices. Many prior art manifolds include complex arrangements of tees, risers and associated valves and connectors. For example in some prior art devices, an individual check valve or stopcock is connected to each inlet riser. These external components make prior art manifolds unsuitable to be placed close to a venipuncture site (for example on a patient's arm). These prior art manifolds must be made relatively large and robust to overcome the inherent fragility of such geometrical arrangements and connections, making separate provisions for supporting the manifold necessary (for example on a stand conventionally used for hanging intravenous fluid reservoirs). Usually, elaborate provisions for protecting the manifold from damaging handling or movement would otherwise need to be made. In such arrangements, tubing lines often are confusingly branched in different directions. The necessity of providing additional support structure on an intravenous infusion hanger stand, for example, with its associated cost, and the inconvenience to medical care personnel in connecting, supporting and protecting such prior art manifolds are undesirable. These problems are especially burdensome in the case of ambulatory patients, who may need to transport the complex infusion set incorporating these features. Otherwise, some of these patients may be able to carry the infusion set about their person. For example, multiple belt-mounted syringe pumps for intravenous infusion can be used.

But on a day-to-day basis, perhaps the most problematic aspect of prior art manifolds is that the relatively large and complex manifold arrangements give rise to dead spaces within the manifold where air may be trapped or fluids may collect. This makes such devices difficult to purge, either of air, or of incompatible fluids. Also, they give rise to large switching volumes (the volume of fluid treat must be displaced through the manifold before a newly selected medicament exits the manifold).

Manifolds used in pharmacological applications also are relatively large, and thus have large switching volumes associated with them. Such devices, being intended for rapid mixing of large volumes of fluids, have considerable dead space. Turbulent mixing associated with their intended use makes such considerations relatively unimportant. However, in low (laminar) flow applications, and particularly in situations where sequential administration of fluids is desired (for example administration of incompatible fluids), the dead spaces associated with these devices makes them unsuitable. Air or fluids may linger in such dead spaces, making the manifold difficult to purge.

Many of the stopcocks used in intravenous infusion sets and associated with manifolds also inherently have dead spaces wherein fluid may collect. For example in stopcocks having a "T" passage valve body, fluid may linger in the unused branch of the "T". These problems can be critical in applications involving small doses of fluid or sequential administration of incompatible fluids.

Moreover, as mentioned above, because of the aforementioned relatively large size and external geometric complexity of the prior art manifolds with their tees, risers, check valves or stopcocks, and couplers connected in angular relationships, they are unsuited to be positioned close to a venipuncture site in a patient. Prior art manifolds are necessarily separated from a venipuncture site on a patient by a relatively long flexible tubing line, as they must be supported by some means, as discussed above. The relatively long line from the manifold to a delivery site on a patient's body inherent in prior art manifolds yields, in addition to the switching volume associated with the manifold itself, a relatively large switching volume associated with the distance a newly selected medicament must travel from the manifold to the delivery site. This later switching volume associated with the fluid tubing line also is undesirable, particularly in low volume infusion applications.

In addition to the foregoing considerations, it is undesirable for medical care personnel, who are often harried, to be confronted by a disorderly and unnecessarily complex intravenous infusion set. In addition to time wasted in setting up, purging of air and maintaining such a complex arrangement, the potential of a life-threatening mistake is increased. This is true both in direct infusion of a patient, and in hospital pharmacy settings.

Lastly, it should be borne in mind that an intravenous fluid manifold is generally disposed of after a single use. Therefore cost considerations are particularly important. Prior art devices, being relatively large and complex, also have associated with them relatively high costs of manufacture, both in terms of labor and materials. Moreover, the aforementioned time wasted by medical care personnel inherent in using complex prior art manifolds may lead to higher costs as well.

As can be appreciated from the forgoing, important considerations in using a manifold in a medical infusion set are that the infusion set should be easily set up, easily purged of air, and easily maintained in use. In such use, the manifold should be configured for efficient flushing between sequential administration of multiple fluids so that incompatible fluids do not mix. It should be reliable and rugged in the patient care environment, and have associated with it small switching volumes to facilitate the administration of very small doses of medicaments.

Hence, those concerned with the development and use of intravenous infusion sets have recognized the need for an improved fluid manifold for use in intravenous infusion sets. Such a manifold would have minimal dead space wherein fluids or air may collect. It would optimally be capable of preventing retrograde flow. Yet the manifold should be small (but not fragile) to minimize switching volumes and to facilitate placement close to a venipuncture site on a patient. Also needed is a fluid manifold that assists in the organization of the flexible tubing lines attached for a compact and orderly configuration. And lastly it is recognized that the fluid manifold must be simply and reliably constructed at low cost. The present invention fulfills these needs and others.

SUMMARY OF THE INVENTION

A manifold for use in medical fluid infusion applications according to principles of the present invention comprises a manifold housing with an upstream inlet, a downstream outlet, and at least one inlet intermediate the upstream inlet and the outlet, and a plurality of retrograde-flow-checked inlet valve seats intermediate the upstream inlet and the outlet. Each of these retrograde-flow-checked valve seats is associated with a selected inlet, chosen to be retrograde flow checked. Within a chamber defined within the manifold housing is disposed a single resilient backcheck member which is urged against said retrograde-flow-checked inlet valve seats to prevent retrograde flow, and yet allows inflow through the individual inlets independent of one another. The retrograde-flow-checked inlet valve seats are positioned at the inlets to the chamber and are flushed by a fluid flowstream flowing through the manifold from the upstream inlet downstream to the outlet. If the upstream inlet is selected, the retrograde-flow-checked inlet valve seat associated with the upstream inlet is flushed by a flowstream from that inlet.

In a more structural aspect, the manifold according to principles of the present invention comprises two housing members which are sealingly joined together confining the single resilient backcheck member between the housing members in a chamber formed therebetween. The chamber is configured to enhance the flushing action of a flowstream through the manifold, cleansing all surfaces and the resilient backcheck member therein even in low flow applications.

A first housing member incorporates a plurality of retrograde-flow-checked inlet valve seats positioned downstream of an upstream manifold inlet and upstream of a downstream manifold outlet, while a second housing member incorporates support members, being protrusions from the housing member into the chamber, centered opposite the retrograde-flow-checked inlet valve seats, which urge the resilient backcheck member against individual inlet valve seats defined by an annular lip of each retrograde-flow-checked inlet. This configuration eliminates the need for external tees, risers, connectors, and the like, thus eliminating the inherent dead spaces and fragility associated with those structures.

The resilient backcheck member is a membrane, flat in its relaxed state, that is thus deformed to slight depressions at the plurality of locations of the retrograde-flow-checked inlets. The membrane backcheck member is symmetrical and reversibly interfits with the housing members without affecting its function so that correct installation is facilitated.

In a further aspect, a manifold according to principles of the present invention is particularly adapted to low volume infusion applications. The structure allows construction of a very small manifold, and placement close to a delivery site, for example a venipuncture site. Small switching volumes are thus achieved. The configuration of the chamber inside the manifold conforms to the shape of the resilient backcheck member thereby directing a flushing flowstream thereon, and minimizes dead spaces where air or fluid may collect. As mentioned, the first or most upstream inlet at an upstream end of the assembled manifold housing can be unselected, and therefore configured such that it is not retrograde flow controlled by the resilient backcheck member. A flushing flowstream of a carrier fluid then transits the manifold unimpeded, into which fluid flow from the individual retrograde flow controlled outlets may be added.

The fluid manifold of the present invention can also incorporate an injection site, to allow insertion of a cannula and injection of another fluid into a flowstream through the manifold. When the most upstream inlet is not retrograde flow checked by means of the resilient back check member, this injection site advantageously can be disposed in a first housing member centered opposite the upstream inlet disposed in a second housing member. This arrangement allows a cannula to be relatively deeply accommodated within the first or upstream inlet thereby stabilizing it.

These and other features and advantages of the invention will become apparent from the following more detailed description, taken in conjunction with the accompanying drawings, which illustrate, by way of example, the features of the invention.

BRIEF DESCRIPTION OF THE DRAWINGS

Like reference characters refer to like or corresponding elements in the several figures of the drawings.

DETAILED DESCRIPTION OF THE PREFERRED EMBODIMENT

Figures 1, 2:
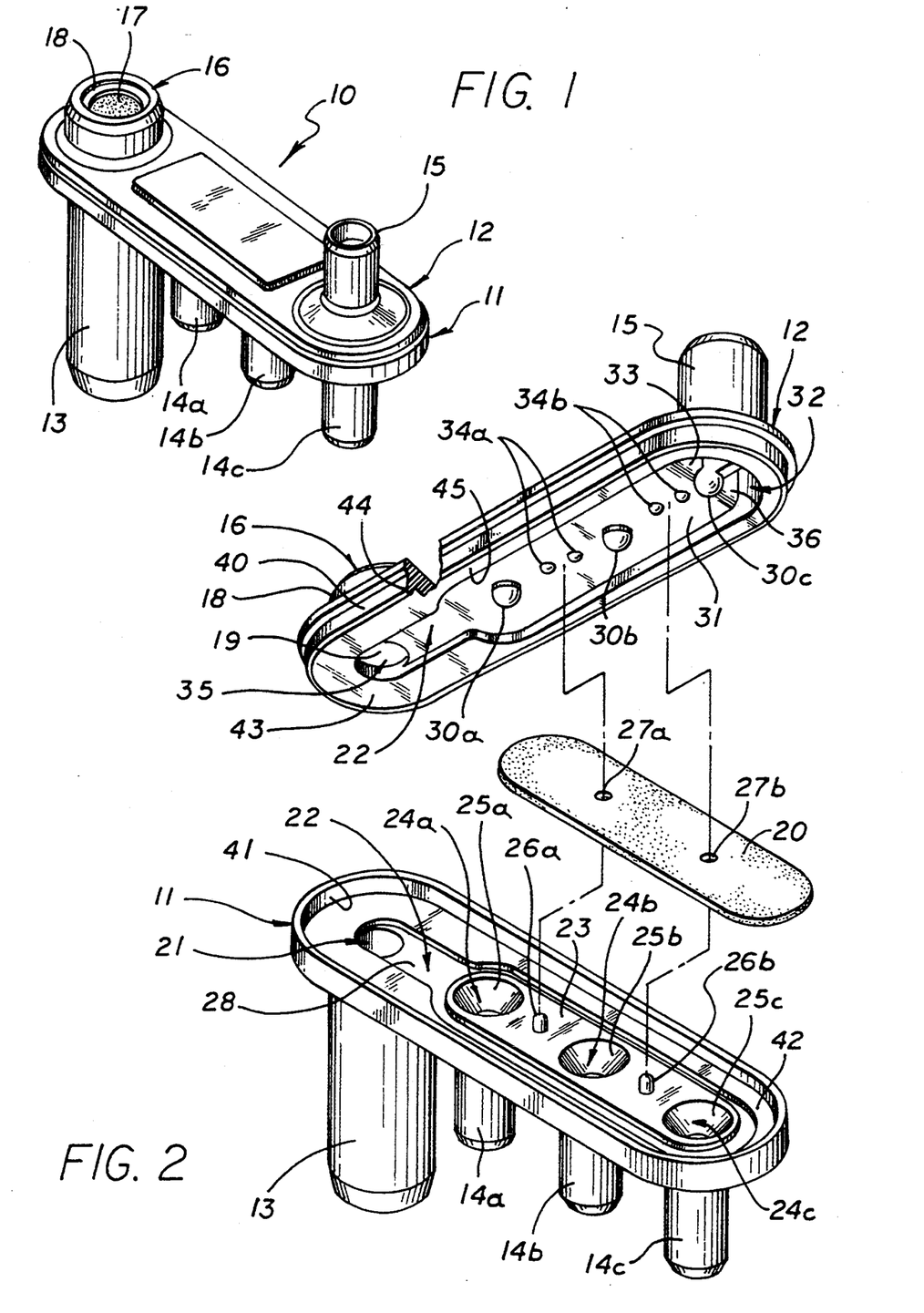
FIG. 1 is an isometric view of a fluid manifold constructed in accordance with principles of the present invention.
FIG. 2 is an exploded isometric view of the fluid manifold of FIG. 1, illustrating the components thereof.

Referring now to FIG. 1 of the exemplary drawings, a fluid manifold 10 according to principles of the present invention comprises an upstream housing member 11 and a downstream housing member 12 which are sealingly mated together to form a compact manifold 10. Differing fluids may be added to the manifold; for example a parenteral fluid through an upstream inlet connector 13, and one or more medicaments through one or more of three retrograde flow controlled inlet connectors 14a, 14b, and 14c, as well as an injection site 16, to be combined in a single flowstream which exits the manifold through an outlet connector 15. The housing members can be formed of a relatively hard and resilient plastic, and are formed of a modified acrylic copolymer in this embodiment. Examples of such a modified acrylic copolymers are Cyrolite TM XT and Cyrolite High Flow TM G-20 manufactured by Cyro Industries of Mt. Arlington, N.J.

The upstream housing member 11 externally embodies inlet connectors 13 and 14a, 14b, 14c, arranged sequentially and in line, while the downstream housing member 12 externally embodies outlet connector 15 and an injection site 16. The injection site externally comprises a resilient self-sealing member 17 fitted in a containment 18. The injection site is opposite the upstream inlet connector 13 allowing cannula penetration to be quite deep, as discussed below. The outlet connector 15, in this embodiment, is disposed opposite the most downstream of the retrograde flow controlled inlet connectors 14c. This inlet opposite outlet arrangement, as well as the injection site opposite inlet arrangement result in a more compact manifold. Moreover, the inlet connectors 13, 14a, 14b, and 14c are all directed in a first direction, while the outlet connector 15 is directed in an opposite direction facilitating organization of connected fluid tubing lines (not shown).

The longitudinal centerlines of the inlet connectors 13 and 14a, 14b, 14c, as well as the outlet connector 15 are all parallel with one another. Additionally, the inlets 13, 14a, 14b, and 14c and the outlet are located in relation to each other so that they are sequential in the flowstream between the most upstream inlet and the downstream outlet. This also contributes to a compact and organized arrangement of connected lines.

In this embodiment, examples of external dimensions are about 1.3 in. (3.3 cm) for an overall elongated dimension and about 0.39 in. (1.0 cm) for an overall transverse dimension. The longest inlet connector (upstream inlet connector 13), for example, may have a length dimension of about 0.6 in. (1.5 cm). This size, in addition to yielding a small switching volume through the manifold, allows placement of the manifold relatively close to a delivery site on a patient, reducing a switching volume associated with the length of a connecting flexible tubing line (not shown) between the manifold and the patient. Weight is decreased, as well as is the cost of materials. This size is made possible by the internal check valve configuration described below and the concomitant elimination of external tees, risers, connectors, valves etc. (further reducing cost). This compactness also makes the manifold less fragile.

Referring to FIG. 2, the two housing members 11 and 12 when connected contain a resilient backcheck member 20 therebetween, which in combination with the upstream housing member 11 and downstream housing member 12 provides a backcheck valve action to prevent retrograde flow through inlet connectors 14a, 14b, and 14c. An upstream inlet 21 is in fluid communication with the upstream inlet connector 13 and a chamber 22 defined within the connected housing members 11 and 12. The chamber is configured such that dead space is minimized. The surfaces of the chamber are given smooth transitions and beveled corner configurations, and the dead spaces associated with prior art devices having tees, risers, or stopcocks for example have been eliminated (with a concomitant reduction in complexity, fragility, weight and cost). Moreover, the interior surfaces defining the chamber are configured so that they can be continuously swept by a flowstream from the most upstream inlet 21 through the chamber 22 to an outlet 32.

Figure 3:
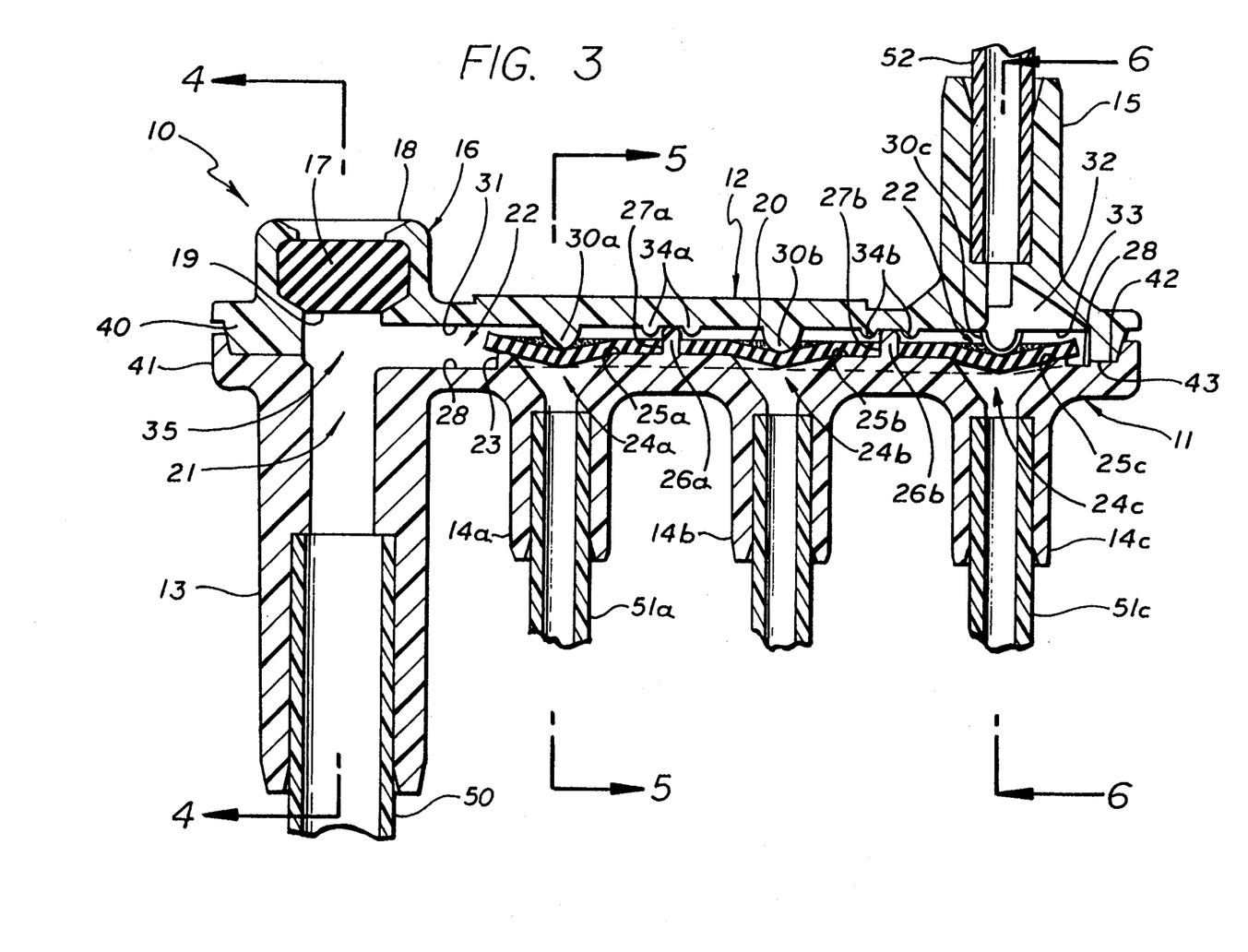
FIG. 3 is a elevational view, in cross-section, of the fluid manifold of FIG. 1.

Referring to FIG. 3, the upstream surface 19 of the resilient self-sealing member 17 of the injection site 16 is also flushed by a flowstream from the upstream inlet 21. In the embodiment shown the flow is directed squarely onto the resilient self-sealing member 17 for this purpose as a result of the coaxial configuration of the injection site and upstream inlet. The resilient self-sealing member 17 is contained within a swage-molded containment member 18. The injection site provided is conventional, and the resilient self-sealing member 17 may be formed of latex, for example. This injection site allows additional medicaments to be introduced to a flowstream through chamber 22 by insertion of a cannula through the resilient self-sealing member 17. The alignment of the injection site inlet 35 and the upstream inlet 21 allows an inserted cannula to be deeply accommodated within inlet 35 and inlet connector 13. The inserted cannula is thus stabilized to some extent against relative lateral displacement or misalignment while inserted.

Referring now to FIGS. 2 and 3, within the chamber 22, and embodied in the upstream housing member 11 a raised portion 23 of an upstream wall surface 28 surrounds the sequentially disposed retrograde-flow-checked inlets 24a, 24b, and 24c. The shape of the raised portion 23 is elongated with parallel sides and rounded ends. The raised portion 23 incorporates the individual retrograde-flow-checked inlet valve seats 25a, 25b, and 25c for each of the individual retrograde-flow-checked inlets at the annular lips of the inlets. The resilient backcheck member 20 seats in sealing contact with these valve seats embodied in the raised portion 23.

The resilient backcheck member 20 is an elastomeric membrane, formed of silicone in this embodiment. A wide range of elastomeric materials may be used, including for example latex or urethane. The backcheck member has a generally flat elongated shape with rounded ends. When installed, the elongated dimension is in the direction of a flowstream through the manifold, so as to cover all the retrograde-flow-checked inlets 24a, 24b and 24c. The upstream and downstream ends are rounded to correspond with the raised portion 23 of the upstream housing wall 28. The resilient backcheck member 20 has the same general shape as the raised portion 23 but is slightly larger to assure coverage of the retrograde-flow-checked inlets. This shape comports with the overall configuration of the chamber 22 which surrounds and conforms to the shape of the resilient backcheck member 20 and the raised portion 23 so that a flowstream through the chamber can flush the resilient backcheck member and the retrograde-flow-checked inlets sequentially embodied in the raised portion.

During use the flushing flowstream sweeps the interior surfaces of the manifold and the resilient backcheck member 20 due to the above-described configuration. Even in very low laminar flow conditions, lingering air or fluids are carried downstream because the flushing flowstream reaches all parts of the chamber 22 wherein dead space is minimized. Thus, the manifold is easily purged. As fluids cannot linger in the manifold, the manifold is particularly adapted to sequential administration of differing fluids. Particularly, this is important in the administration of incompatible fluids.

The resilient backcheck member 20 is symmetrical in overall shape, and has alignment appatures which, in this embodiment, take the form of two holes 27a, and 27b. The holes are aligned on a longitudinal central axis, and are also symmetrically spaced from the center of the resilient backcheck member 20. The resilient backcheck member is placed upon, and constrained from sideways (radial plane) motion by alignment studs 26a and 26b which engage holes 27a and 27b. These alignment studs protrude from the raised portion 23 of upstream wall surface 28 intermediate and in line with the retrograde flow controlled inlet openings 24a, 24b,and 24c. The alignment studs 26a and 26b and the holes 27a and 27b, being thus symmetrically aligned and centered, allow the resilient backcheck member 20 to be reversibly interfit with the housing member 11 in either of two possible opposite orientations about the three mutually orthogonal axes defining geometrical space, without affecting its function. (Thus it can be installed without regard to front or back and right or left and top or bottom.) This simplifies and speeds assembly and also enhances reliability of the backcheck action of the resilient backcheck member at the individual retrograde-flow-checked inlets, reducing costs.

When the downstream member 12 is mated with the upstream housing member 11, the resilient backcheck member 20 is urged against the valve seats 25a, 25b, and 25c by support members 30a, 30b, and 30c which protrude from the downstream wall 31 of the chamber 22. Each of these support members is centered on and coaxial with a retrograde flow controlled inlet opening 24a, 24b, or 24c. (This can more easily be seen in FIGS. 3, 5 and 6.) Again referring to FIGS. 2 and 3, the support members are of a length such that the resilient backcheck member 20 is dimpled into each of the retrograde flow controlled inlets. The resilient backcheck member 20 is thus elastically deformed and biased into sealing contact with retrograde-flow-checked inlet valve seats 25a, 25b, and 25c.

The resilient backcheck member 20 prevents fluid from the chamber 22 from entering the retrograde-flow-checked inlets 24a, 24b, and 24c. Fluids can only enter the chamber from any of the retrograde-flow-checked inlets when the fluid pressure in a particular individual inlet exceeds the fluid pressure in the chamber by an amount sufficient to overcome the biasing force urging the resilient backcheck member 20 against the particular valve seat 25a, 25b or 25c. Thus the resilient backcheck member 20 is only displaced from the individual valve seats to allow flow through the respective inlet openings when the pressure differential is greater than the cracking pressure associated with the resilient backcheck member 20 (the fluid pressure in the retrograde-flow-checked inlets being greater than that in the chamber 22). This pressure differential would prevent retrograde flow. Check valve action at each of the retrograde-flow-checked inlets is independent of that at the other retrograde-flow-checked inlets, depending only on the relative fluid pressure within the individual retrograde flow controlled inlet 24a, 24b or 24c, and the chamber 22.

By obviating the need for externally connected individual check valves for each inlet, the above described overall configuration of a manifold in accordance with the principles of the invention greatly reduces the external geometrical complexity of the manifold and eliminates more expensive components. Cost savings are realized in terms of materials and assembly costs. These savings are in addition to time saved formerly spent purging air or incompatible fluids from risers, connectors, valves, etc. or sorting out confusingly branched connected fluid tubing lines in prior devices.

The plate thickness of the resilient backcheck member is selected to give, in combination with the amount of dimple imparted by the support members 30a, 30b, and 30c, the desired cracking pressure for the retrograde-flow-checked inlets 24a, 24b, 24c. In this embodiment it can be from about 0.01 in (0.025 cm) to about 0.025 in. (0.064 cm) thick. The resulting cracking pressure will be about 0.3 psi ($2.0 \times 10^3$ Pa) to about 30 psi ($2.0 \times 10^5$ Pa). As an example, a thickness of about 0.015 in. (0.038 cm) can be used to obtain a cracking pressure of about 1.2 psi ($8.3 \times 10^3$ Pa) to about 2.0 psi ($14.0 \times 10^3$ Pa). These cracking pressures are adapted for advantageous use of a gravity fed flowstream (of parenteral fluid for example) through the manifold 10 from a flexible tubing line 50 connected to upstream inlet 21, with pumped or syringe forced delivery of fluids through the flexible tubing lines 51a, 51b, 51c connected to the retrograde-flow-checked inlets 24a, 24b, and 24c. In this embodiment a check valve of lower cracking pressure adapted for gravity feed (not shown) can be employed in the flexible tubing line 50 upstream of the upstream inlet connector 13 to prevent reverse (reflux) flow through the manifold 10.

Continuing now with a description of the structure, the most downstream of the support members 30c is centered over the most downstream retrograde flow controlled inlet 24c, and an outlet 32 of the chamber 22. This support member 30c differs from the two more upstream support members, 30a and 30b, in that in addition to protruding from the downstream wall 31 of the chamber, it is incorporated into an outlet bridge member 33 that traverses the outlet 32, buttressing the downstream side of the downstream support member 30c. This arrangement allows the outlet to be coaxial with and oppositely directed to downstream retrograde flow controlled inlet 24c for more compactness, and to assist in organization of connected tubing lines 50, 51a, 51b, 51c and 52 as before described.

A downstream end portion 36 of a downstream wall 31 of the chamber 22 is given a curving shape to provide a smooth hydraulic transition into the outlet 32. The outlet 32 is semi-frustoconically shaped, in that the downstream end portion 36 of the downstream wall 31 of the chamber 22 extends into the frustoconical configuration of the outlet 32 such that the opening of the outlet 32 is generally semicircular in shape. This results in the outlet 32 having a generally semi-frustoconical shape.

This configuration cooperates with the shape of the chamber 22 which follows the semicircular contour of the downstream end of the resilient backcheck member, to direct a flowstream through the manifold around and past the downstream end of the resilient backcheck member 20 for enhanced flushing thereof, and to improve flow characteristics at the outlet. Due to this configuration recirculation and dead spaces are minimized. Even though the outlet 32 is coaxial with the most downstream retrograde-flow-checked inlet 24c, fluid is directed past the downstream end of the resilient backcheck member 20 and then into the outlet 32 for example by the portion of the chamber 22 near the upstream wall 28 at the downstream end. There the upstream wall 28 in combination with the other surfaces of the chamber 22 and the resilient backcheck member 20 directs fluid past the portion of the resilient backcheck member where its sides are parallel, and then smoothly transitions to be nearly co-planer with the raised portion 23 of the upstream wall 28. This directs fluid radially out and around the downstream end of the resilient backcheck member 20 toward the outlet 32. Even at very low flows the surfaces of the chamber at the downstream end are swept due to this configuration.

As mentioned, the outlet 32 is also bridged by a bridge member 33. This bridge member serves to support the most downstream support member 30c of the check valve system associated with the retrograde-flow-checked inlets 24a, 24b, and 24c. The bridge member 33 also serves to prevent the downstream end of the resilient backcheck member 20 from occluding the outlet 32. The shape of the bridge member 33 at a downstream end portion 37 is a square cut-out shape to provide for increased flow at the downstream end of the semi-frustoconically shaped outlet 32 as the outlet 32 narrows. This square cut-out can more easily be seen in FIG. 3.

Intermediate and in line with the three support members 30a, 30b, and 30c are two sets of buttons 34a and 34b which protrude from the downstream chamber wall 31. The alignment studs 26a and 26b nearly touch the downstream chamber wall 31 between the two buttons in each button set 34a and 34b when the two housing members 11 and 12 are connected together. These button sets keep the resilient backcheck member 20 (which can move up and down the alignment studs during use) away from the chamber wall 31 to assure that a flushing flowstream can flow therebetween.

The upstream housing member 11 and downstream housing member 12 are sealingly joined by the interaction of a wall member 40 and a shoulder member surface 43 on the downstream housing member 12, and a wall member 41 and a shoulder member surface 42 on the upstream housing member 11. Wall members 40 and 41 are given complementary interior slopes to help align the two housing portions during assembly. The outer periphery of shoulder member surface 43 on the downstream housing member is provided with an energy director 44, which is conventional, to aid in ultrasonically welding the two housing members together in a conventional manner. Other embodiments include sealing the housing members together by heat or solvent welding, or adhesives, wherein an energy director would not be required.

Referring more particularly to FIG. 3, a length of tubing 50 connected to the upstream inlet 21 by upstream inlet connector 13 conveys a first fluid downstream to pass through inlet 21 into the chamber 22. The tubing can be connected to a fluid reservoir (not shown) for gravity feed and may incorporate a check valve (not shown) disposed in engagement with the length of tubing 50 upstream of the manifold 10 as before described. The tubing 50 is conventionally held in upstream inlet connector 13 by a combination of friction fit and adhesives or solvent bonding.

Individual lengths of tubing, (51a, 51b and 51c) are likewise connected to each of the retrograde-flow-checked inlets 24a, 24b, and 24c by retrograde flow controlled inlet connectors 14a, 14b, and 14c. Thus second, third and fourth fluids, conveyed by these lengths of tubing 51a, 51b, 51c, can be made to pass through retrograde-flow-checked inlets 24a, 24b, 24c. These fluids can be delivered for example by peristaltic infusion pumps, syringe pumps, and manual actuation of syringes connected to these lengths of tubing (not shown). Fluid delivery can be, for example, sequential, pulsed, simultaneous or some combination thereof.

When individually controlled pressure delivery of these various fluids through retrograde-flow-checked inlets 24a, 24b, 24c forces the resilient backcheck member 20 away from valve seats 25a, 25b and/or 25c, the fluids pass between the valve seat 25a, 25b and/or 25c and the resilient backcheck member 20 into the chamber 22. For each inlet, this can only happen when fluid pressure within the inlet 24a, 24b, 24c is greater than the fluid pressure in the chamber 22 by amount greater than the cracking pressure as before described. The resilient backcheck member 20 can locally deform elastically to allow one or more of the retrograde-flow-checked inlets 24a, 24b, and/or 24c to be open when others are closed. All retrograde-flow-checked inlets could also be open simultaneously.

In this embodiment the manifold 10 is particularly adapted to having the most upstream inlet 21 connected to a gravity feed fluid source (not shown) for a flow-through carrier stream, of parenteral fluid for example, through the manifold 10. Other medicaments can be added through the retrograde flow controlled inlets 24a, 24b, 24c by pressure feed as before discussed, for example by use of syringes in administration of anesthetic in an operating room procedure. In this connection, the upstream inlet 21 and upstream inlet connector 13 are of a relatively larger diameter than the retrograde flow controlled inlets to allow relatively greater flow therethrough. Because of the flushing configuration of the manifold, however, less carrier fluid is required to deliver a given dose of medicaments than that inherent in previous devices.

In another embodiment the retrograde-flow-checked inlets could be connected to fluid sources that involve gravity feed. The cracking pressure corresponding to the amount of dimpling and other resilient backcheck member 20 parameters, as described above, are adjusted to yield a conventional cracking pressure value for a gravity feed application.

Continuing with discussion of the illustrated embodiment, fluids introduced through the inlets 21 and 24a, 24b, and 24c pass through chamber 22 as they flow downstream and through outlet 32 into a length of tubing 52 connected to outlet 32 by outlet connector 15 in the manner described above for inlet connectors 13 and 14a, 14b, 14c. The length of tubing 52 is in turn connected to a delivery site, for example a venipuncture site in a patient (not shown). As mentioned, because a manifold constructed in accordance with the principles of the invention may be relatively small, light weight and rugged, it may be mounted on the arm of a patient, for example, even at the delivery site. Therefore, the sequential or simultaneous infusion of various differing fluids for intravenous infusion may be accomplished with very little switching volume associated with the length of tubing 52 connected to the outlet 34 by outlet connector 15. Particularly, small doses of medicaments can conveniently be administered with a correspondingly small amount of carrier fluid (parenteral fluid, for example).

As a result of the inlet connectors 13, 14a, 14b, and 14c being directed in a common single direction and spaced relatively close together as before described, the multiple upstream fluid conveying tubing lengths 50 and 51a, 51b, 51c can be bundled together for some distance upstream (not shown). This further enhances a compact arrangement of the various tubings connected to diverse fluid sources for efficient patient care. The risk of disconnection of individual lines is reduced. These considerations can be important for example where the patient is ambulatory, or in an operating room setting where a simplified and compact set is very desirable.

In yet another embodiment the downstream tubing line 52 may be connected to a fluid reservoir (not shown) and the manifold 10 connected as described above to various fluid sources for preparing a mixed fluid solution in the fluid reservoir connected to tubing line 52. The reservoir when thus filled with mixed fluids can then be disconnected and sealed. The mixed fluids can then be later infused into a patient.

Figure 4:
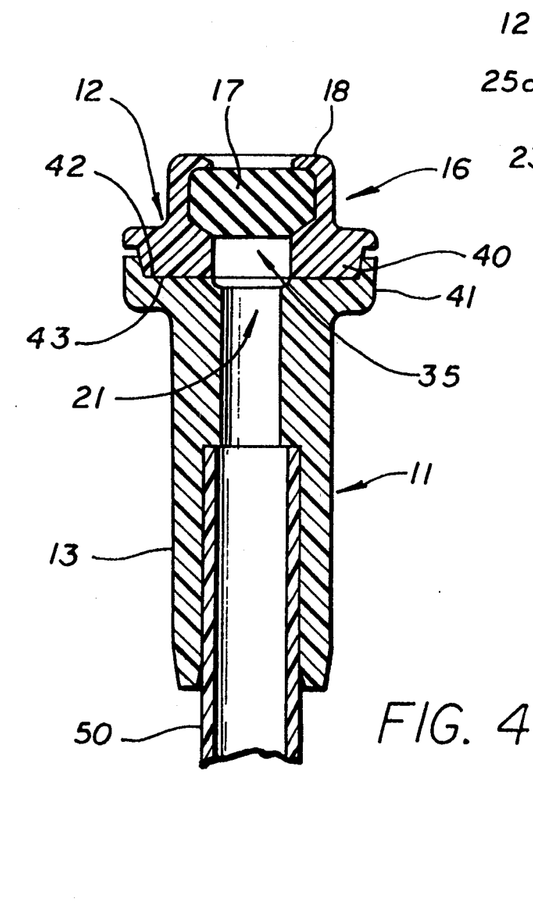
FIGS. 4, 5 and 6 are elevational views, in cross-section, of the fluid manifold taken along lines 4—4, 5—5 and 6—6, respectively, in FIG. 3.
Figures 5, 6:
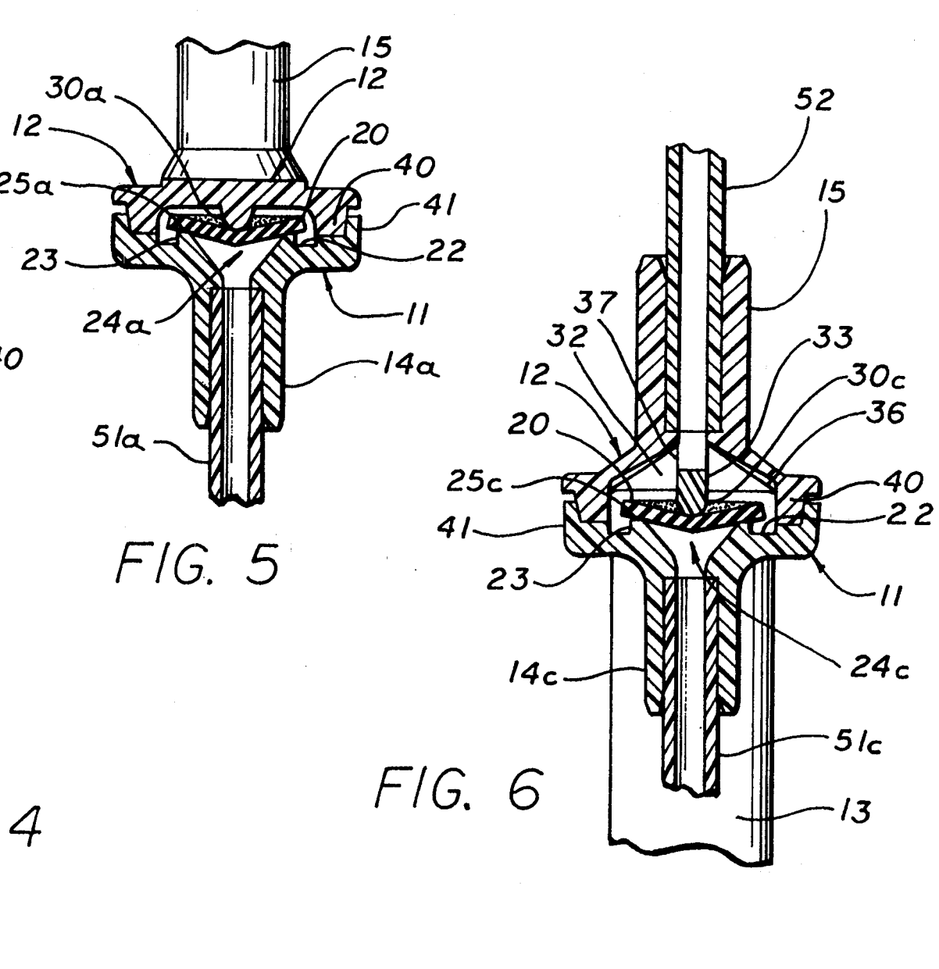

As can be seen in FIG. 3, taken together with the cross-sectional views of FIGS. 4, 5 and 6, the cross-sectional area of the chamber 22 within the fluid manifold 10 is substantially constant. However, the upstream inlet 21 is slightly smaller in cross-sectional area than that of upstream flexible tubing 50. The cross-sectional area of the chamber 22 at a point downstream of the upstream inlet, for example, in the area of cross-section 5—5 shown in FIGS. 3 and 5, is slightly smaller still. The cross-sectional area of the downstream end of the frustoconical outlet 32 in the area of the cut out portion 37 of the outlet bridge member 33 is smallest, yet greater than the cross-sectional area of the interior lumen of the downstream tubing connected to the outlet 52. This configuration enhances the flushing action of a flowstream through the manifold even at very low flow rates.

Referring particularly to FIG. 5, the shape of the interior surfaces defining the chamber 22 cooperate with other elements of the manifold (for example alignment studs 26a and 26b) to prevent a mischeck condition wherein the resilient backcheck member 20 is laterally displaced enough to allow retrograde flow of fluid past an annular valve seat 25a, 25b or 25c into the retrograde flow controlled inlet 24a, 24b, or 24c. The distance from the edges of the resilient backcheck member to the downstream chamber wall surface 31 is such that if one edge of the resilient backcheck member were to abut the chamber wall surface 31, the opposite edge would still be beyond the annular lips of the valve seats 25a, 25b, and 25c. Thus the valve seats 25a, 25b and 25c of the retrograde-flow-checked inlets are always covered by the resilient backcheck member 20.

Lastly, from FIG. 3 taken together with FIGS. 4, 5 and 6, the simple functional arrangement of the various elements, including those providing check valve action at the retrograde-flow-checked inlets 24a, 24b, 24c can be appreciated. This arrangement provides reliable check valve action due to the assured cracking pressure required to overcome the elastomeric bias of the resilient backcheck member 20 against the individual valve seats 25a, 25b and 25c engendered by support members 30a, 30b, and 30c. The resilient backcheck member 20 is positively located in the correct position by interaction of alignment holes 27a and 27b and alignment studs 26a and 26b, as well as interior surfaces of the chamber 22. Yet, as can best be appreciated from FIG. 2 the fluid manifold 10 is simple in construction and easily assembled.

From the foregoing, it will be appreciated that the fluid manifold according to principles of the present invention provides reliable interconnection of sources of differing fluids, for example medicaments, for simultaneous infusion or sequential infusion without cross-contamination or other problems associated with dead spaces. These desirable functions are combined in a compact structure convenient for intravenous infusion environments. The manifold is particularly suited to low volume infusion applications. Further, these advantages are obtained in a device that is easily assembled at low cost.

While a particular form of the invention has been illustrated and described, it will be apparent that various modifications can be made without departing from the spirit and scope of the invention.

What is claimed is:

1. A fluid manifold for use in intravenous infusion applications adapted for fluid flow therethrough in a direction from an upstream inlet at an upstream end to a downstream outlet at a downstream end, comprising:

a) a first inlet housing member having an upstream inlet, and a plurality of sequentially disposed retrograde-flow-checked inlets downstream thereof having annular valve seats, and a plurality of alignment studs for locating a resilient backcheck member;

b) a second housing member sealingly mated to the first housing member having an injection site formed therein coaxial with the upstream inlet, and having support members for urging a resilient backcheck member against the annular valve seats of the retrograde-flow-checked inlets;

c) a resilient backcheck member adapted to be reversibly disposed on the alignment studs of the first housing member and which is urged against and sealingly abuts the valve seats of the retrograde-flow-checked inlets embodied in the first housing member to provide individual retrograde flow control to each of the retrograde-flow-checked inlets by allowing fluid flow past the individual annular valve seats of a particular individual retrograde flow controlled inlet into the chamber only when fluid pressure in that individual retrograde flow controlled inlet exceeds that of the chamber by a preselected cracking pressure, wherein the upstream and downstream housing members have inner surfaces that form a chamber within the manifold housing that conforms to the periphery of the resilient backcheck member directing a fluid flowstream transiting the manifold from the upstream inlet to the downstream outlet into flushing contact with the resilient backcheck member and valve seats of the retrograde-flow-checked inlets.

2. A fluid manifold for use in infusing medical fluids, comprising:

a housing having an upstream inlet and a downstream outlet and at least one retrograde flow control inlet intermediate the upstream inlet and the outlet, and a plurality of retrograde-flow-checked valve seats, each such valve seat associated with at least one retrograde flow control inlet, and a chamber interconnecting the inlets and the outlet;

a single resilient backcheck member confined within the chamber and deformably urged against a plurality of the retrograde-flow-checked valve seats providing individual check valve action at each of the plurality of retrograde-flow-checked valve seats;

an injection site formed in the housing opposite an inlet such that it is in fluid connection with the chamber;

wherein the housing comprises support members disposed to urge the resilient backcheck member against the retrograde-flow-checked valve seats.

3. A fluid manifold for use in infusing medical fluids, comprising:

a housing having an upstream inlet and a downstream outlet and at least one inlet intermediate the upstream inlet and the outlet, and a plurality of retrograde-flow-checked valve seats, each such valve seat associated with a selected inlet, and a chamber interconnecting the inlets and the outlet;

a single resilient backcheck member confined within the chamber and deformably urged against a plurality of the retrograde-flow-checked valve seats providing individual check valve action at each of the plurality of retrograde-flow-checked valve seats;

wherein the housing comprises support members disposed to urge the resilient backcheck member against the retrograde-flow-checked valve seats, and wherein the chamber within the manifold is of relatively constant cross-sectional area which is smaller than the cross-sectional area of the upstream inlet and larger than the cross-sectional area of the downstream outlet at a downstream end thereof.

4. A fluid manifold for use in infusing medical fluids having a chamber formed therein, and a flowstream therethrough directed from a most upstream inlet to a downstream outlet, comprising:

a) a first housing member incorporating a plurality of retrograde flow checked inlets including a most upstream inlet, and a plurality of retrograde-flow-checked inlet valve seats, each such valve seat being associated with a selected inlet, wherein the retrograde-flow-checked inlet valve seats are disposed within the chamber where they are continuously flushed by the flowstream, b) a second housing member sealingly coupled to the first housing member with support members positioned opposite and centrally to the retrograde-flow-checked inlets and an outlet positioned downstream of the support members, c) a resilient backcheck member confined between the first and second housing members, wherein the support members urge the resilient backcheck member against the retrograde-flow-checked valve seats to provide a backcheck action to prevent retrograde flow past said retrograde-flow-checked inlet valve seats and yet independently allow downstream flow through each of the individual inlets, and wherein the chamber surrounds and follows the contour of the periphery of the resilient backcheck member so that the retrograde-flow-checked inlet valve seats in the chamber are continuously flushed by the fluid flowstream transiting the manifold from the upstream inlet through the downstream outlet and wherein surfaces defining the chamber are provided with smooth transitions and overall configuration that directs the fluid flow onto and around the surfaces to flush fluid therefrom, and wherein the chamber has a relatively constant cross-sectional area smaller in comparison with the cross-sectional area of the upstream inlet.

5. A fluid manifold for use in infusing medical fluids having a chamber formed therein, and a flowstream therethrough directed from a most upstream inlet to a downstream outlet, comprising:

a) a first housing member incorporating a plurality of retrograde flow checked inlets including a most upstream inlet, and a plurality of retrograde-flow-checked inlet valve seats, each such valve seat being associated with a selected inlet, wherein the retrograde-flow-checked inlet valve seats are disposed within the chamber where they are continuously flushed by the flowstream, b) a second housing member sealingly coupled to the first housing member with support members positioned opposite and centrally to the retrograde-flow-checked inlets and an outlet positioned downstream of the support members, c) a resilient backcheck member confined between the first and second housing members, wherein the support members urge the resilient backcheck member against the retrograde-flow-checked valve seats to provide a backcheck action to prevent retrograde flow past said retrograde-flow-checked inlet valve seats and yet independently allow downstream flow through each of the individual inlets, and wherein the resilient backcheck member comprises a symmetrical plate formed of elastic material which interfits with a housing member, and when reversibly interfit with a housing member the resilient backcheck member is correctly positioned relative to the retrograde-flow-checked inlets regardless of its orientation, and wherein the resilient backcheck member is constrained from lateral movement by alignment studs which interfit with at least two openings in the resilient backcheck member.

* * * * *